United States Patent
Denker et al.

(10) Patent No.: US 8,255,054 B2
(45) Date of Patent: Aug. 28, 2012

(54) MRI COMPATIBLE IMPLANTED ELECTRONIC MEDICAL DEVICE

(75) Inventors: Stephen Denker, Mequon, WI (US); Arthur J. Beutler, Greendale, WI (US); Cherik Bulkes, Sussex, WI (US)

(73) Assignee: Kenergy, Inc., Mequon, WI (US)

( * ) Notice: Subject to any disclaimer, the term of this patent is extended or adjusted under 35 U.S.C. 154(b) by 1477 days.

(21) Appl. No.: 11/553,228

(22) Filed: Oct. 26, 2006

(65) Prior Publication Data

US 2007/0106332 A1    May 10, 2007

Related U.S. Application Data

(60) Provisional application No. 60/734,018, filed on Nov. 4, 2005.

(51) Int. Cl.
*A61N 1/375* (2006.01)
(52) U.S. Cl. .......... 607/36; 600/411; 250/515.1
(58) Field of Classification Search .......... 607/36; 600/411
See application file for complete search history.

(56) References Cited

U.S. PATENT DOCUMENTS

| | | | |
|---|---|---|---|
| 2,966,640 A * | 12/1960 | Eiland, Jr. .......... | 333/26 |
| 4,071,032 A * | 1/1978 | Schulman .......... | 607/36 |
| 4,642,569 A * | 2/1987 | Hayes et al. .......... | 324/318 |
| 5,217,010 A * | 6/1993 | Tsitlik et al. .......... | 607/9 |
| 7,003,350 B2 | 2/2006 | Denker et al. | |
| 7,048,716 B1 * | 5/2006 | Kucharczyk et al. .... | 604/164.01 |
| 7,050,855 B2 | 5/2006 | Zeijlemaker et al. | |
| 7,076,283 B2 | 7/2006 | Cho | |
| 7,493,167 B2 | 2/2009 | Hussein et al. | |
| 2001/0035504 A1 * | 11/2001 | Hayes .......... | 250/515.1 |
| 2002/0038135 A1 | 3/2002 | Connelly et al. | |
| 2003/0050557 A1 * | 3/2003 | Susil et al. .......... | 600/424 |
| 2003/0144719 A1 | 7/2003 | Zeijlemaker | |
| 2003/0144720 A1 | 7/2003 | Villaseca et al. | |
| 2003/0144721 A1 * | 7/2003 | Villaseca et al. .......... | 607/122 |
| 2003/0204217 A1 | 10/2003 | Greatbatch | |
| 2004/0088012 A1 | 5/2004 | Kroll et al. | |

(Continued)

FOREIGN PATENT DOCUMENTS

WO    WO 01/78089    12/1992

(Continued)

OTHER PUBLICATIONS

Schenck, Role of magnetic susceptibility in magnetic response imaging: MRI magnetic compatibility of the first and second kinds, Med. Phys. 23 (6), p. 815-850, Jun. 1996.

(Continued)

*Primary Examiner* — Niketa Patel
*Assistant Examiner* — Joseph Stoklosa
(74) *Attorney, Agent, or Firm* — Quarles & Brady, LLP; George E. Haas

(57) ABSTRACT

An implantable electronic medical device is compatible with a magnetic resonance imaging (MRI) scanner. The device has a housing with exterior walls, each formed by a dielectric substrate with electrically conductive layers on interior and exterior surfaces. A series of slots divide each layer into segments. Segmenting the layers provides high impedance to eddy currents produced by fields of the MRI scanner, while capacitive coupling of the segments provides radio frequency shielding for components inside the housing. Electrical leads extending from the housing have a pair of coaxially arranged conductors and traps that attenuate currents induced in the conductors by the fields of the MRI scanner.

23 Claims, 2 Drawing Sheets

U.S. PATENT DOCUMENTS

| | | |
|---|---|---|
| 2005/0043761 A1 | 2/2005 | Connelly et al. |
| 2005/0070972 A1 | 3/2005 | Wahlstrand et al. |
| 2005/0113876 A1 | 5/2005 | Weiner et al. |
| 2005/0187584 A1 | 8/2005 | Denker et al. |
| 2005/0197677 A1 | 9/2005 | Stevenson |
| 2005/0222642 A1 | 10/2005 | Przybyszewski et al. |
| 2005/0222647 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0288743 A1 | 12/2005 | Ahn et al. |

FOREIGN PATENT DOCUMENTS

| | | |
|---|---|---|
| WO | WO 92/21286 | 12/1992 |
| WO | WO 03/063954 | 8/2003 |

OTHER PUBLICATIONS

Nair et al., Magnetic Resonance Imaging In Patients with ICD's and Pacemakers, Indian Pacing and Electrophysiology Journal, vol. 5(3), p. 197-209, (2005).

* cited by examiner

US 8,255,054 B2

MRI COMPATIBLE IMPLANTED ELECTRONIC MEDICAL DEVICE

CROSS-REFERENCE TO RELATED APPLICATIONS

This application claims benefit of U.S. Provisional Patent Application No. 60/734,018 filed Nov. 4, 2005.

STATEMENT REGARDING FEDERALLY SPONSORED RESEARCH OR DEVELOPMENT

Not Applicable

BACKGROUND OF THE INVENTION

1. Field of the Invention

The present invention relates implantable electronic medical devices, such as cardiac pacemakers and defibrillators for example, for stimulating tissue of animal for the therapeutic purposes, and such implantable medical devices that are compatible with magnetic resonance imaging (MRI).

2. Description of the Related Art

Numerous medical conditions, such a cardiac and neurological dysfunctions, are treated by an implanted electronic device which provides electrical stimulation to the affected tissue of the animal. These devices have a plurality of metal components, including the outer case and wire leads extending from the case to electrodes in contact with the tissue to be stimulated.

Magnetic resonance imaging (MRI) is commonly employed to view internal organs of medical patients. To create an image, the patient is placed into very strong magnetic and radio frequency (RF) fields and thus MRI generally is prohibited for patients with implanted ferromagnetic objects. Although it is feasible to minimize and even eliminate the use of ferromagnetic materials in implanted apparatus, electronic devices, such as cardiac pacemakers and defibrillators, require electrically conductive components that are affected by the fields produced by an MRI scanner.

It has been a long-standing goal to make implanted devices MRI compatible so that this imaging modality can be used with patients having those devices. There are several reasons for achieving this goal. First, incompatible implant components induce susceptibility difference, which destroys DC magnetic field homogeneity, thereby affecting the imaging performance of the magnetic resonance scanner. Second, conductive materials present an opportunity for eddy currents to form, which currents generate heat that adversely affects patient safety and degrade the scanner performance by field distortion. Third, the MRI fields may ruin the implanted device. Fourth, the incompatible implant material can potentially cause serious internal injuries to the patient.

The issue of MRI interaction with electronics of an implanted device has to be considered in an integrated fashion to provide compatibility. Table 1 below shows combinations of interactions that are briefly discussed hereinafter.

TABLE 1

Interactions of factors influencing MRI compatibility of an implanted device or component

|  | Patient Safety | Effect on the Implanted Device | Effect on the MR Image |
| --- | --- | --- | --- |
| DC Magnetic Fields | I | II | III |
| Gradient Magnetic Fields | IV | V | VI |
| RF Fields | VII | VIII | IX |

I. Any ferromagnetic material inside the implanted device exposed to the MRI fields experiences a force and a torque, the amount of which depends on the shape, dimensions, and amount of ferromagnetic material. The forces are greatest in areas where there is a gradient in the magnetic field, e.g. upon entering a MRI system. Obviously the surrounding tissue adjacent the implantable device will be damaged in this case, and the health of the patient will be compromised. In addition, metallic components can become hot and burn the patient.

II. Due to MRI field induced torque and movement of the implant, its components may become disconnected making the device inoperable. Ferrites and other ferromagnetic material in transformer cores, inductors and other electronic components become saturated, thereby jeopardizing the function of the medical device. Heating causes electronic components to operate out of specification.

III. The homogeneity of the magnetic resonance imager's DC magnetic field will be distorted, destroying spectral resolution and geometric uniformity of the image. The inhomogeneous field also results in rapid de-phasing of the signal inside the excited volume of the patient. The resultant image shows a distorted view of the patient's anatomy.

Even if the implanted device does not contain any ferromagnetic materials, the magnetic susceptibility of the device may be different than that of the surrounding tissue, giving rise to local distortion and signal dropouts in the image, close to the device. This is especially true for pulse sequences that are sensitive to phase, like echo planar imaging IV. Switching field gradients create large eddy currents, at frequencies up to a few kilohertz, in the metallic housing of an implantable device and any metallic part that forms a loop, such as cables forming a loop. These eddy currents make the device move with the same frequency as the leading and trailing edges of gradient pulses. This movement can be unsafe for the surrounding tissue. The associated eddy current pattern creates local pulsating E-fields, in addition to the E-field generated by the MRI scanner's gradient coil, which can stimulate the patient's nerves. Resultant muscle twitching can be so intense as to be painful.

V. The eddy currents may be strong enough to damage electronic circuits and destroy the implanted device. The pulsating forces on the device may disconnect components.

VI. The eddy currents affect the rise time of the MRI gradient pulses, and therefore affect the minimum obtainable echo time, necessary for many pulse sequences. The eddy currents also locally distort the linearity of the gradient fields and de-phase the spin system, resulting in image distortion and signal dropouts. Phase and frequency encoding of the signal strongly depends on the linearity of the gradients.

VII. The RF field interacts with any metallic part in the device, be it either in the form of a loop, which results in B-field coupling, or a straight conductor, which results in E-field coupling. The B-field component of the RF field can induce currents and voltages in conducting loops. The amplitude depends on the impedance of the loop at the RF frequency, and the size of the loop. An example may be two coaxial cables that form a loop together. Such a loop may have high impedance at DC due to the insulating outer shell of the coax, but the distance between the cables at the crossover point may be equivalent to just the right amount of capacitance to make the loop resonant at the RF frequency.

The E-field component of the RF field will induce voltages and currents in straight conductors, like a single cable for example. The amplitude of the induced voltages and currents depends on the phase length of the conductor, or path, at the associated radio frequency.

The induced voltages and currents create locally very strong E-fields that can burn the patient.

Non-metallic implantable devices do not have these issues, but can still distort the uniformity of the RF field if the permittivity of the device is different than that of the surrounding tissue. This distortion is especially strong at radio frequencies above 100 MHz.

VIII. Localized high voltages and currents in the medical device may cause components to fail either due to high voltage arcing, or due to dissipated power and heat. This includes connections that become unsoldered due to the heat. The device may generate pulsed voltages at unwanted times and locations in the leads of a cardiac pacemaker.

IX. Local distortion of the uniformity of the B-field component of the RF field will give rise to flip angle variation and creates contrast and signal-to-noise-ratio (SNR) inhomogeneity. The specific absorption rate, which is defined as the RF power absorbed per unit of mass of an object, can exceed legal limits. If the specific absorption rate exceeds legal limits, images cannot be made using magnetic resonance scanners.

Therefore it is desirable to provide an integrated, comprehensive solution to MRI compatibility of an implanted medical device that contains electronics circuitry.

SUMMARY OF THE INVENTION

The present implantable electronic medical device is compatible with magnetic resonance imaging and specifically with direct current (DC) magnetic fields, gradient magnetic fields, and RF fields produced by an MRI scanner. This invention offers a comprehensive solution by providing a compatible housing for the medical device and immunizing external cables from currents induced by the MRI fields.

The implantable medical device comprises a housing containing an electronic circuit and having a plurality of exterior walls. Each exterior wall includes a substrate of an electrically non-conductive, dielectric material with an outer surface and an inner surface. A first layer of electrically conductive material is on the outer surface and has a plurality of first slots therein, which expose the dielectric material and divide the first layer into a plurality of first segments. A second layer of electrically conductive material is on the inner surface and has a plurality of second slots therein, which expose the dielectric material and divide the second layer into a plurality of second segments.

The first and second slots preferably are offset from each other so that the first segments overlap the second segments resulting in capacitive coupling of the first and second segments at radio frequencies. This arrangement forms a wall that inhibits low frequency induced eddy currents from being induced by the fields of the MRI scanner, while still shielding components inside the housing from exterior radio frequency signals.

Another aspect of the invention is to make a cable of the medical device also resistant to currents being induced by the MRI fields. This cable extends outside the housing and has a first conductor and a second conductor. A plurality of traps are connected to the second conductor at intervals along the cable. Each trap mitigates electrical currents induced in the cable by one or more fields of the magnetic resonance imaging scanner. Each trap comprises either a choke, a bazooka balun, PIN diode, or a micro electromechanical system switch.

DETAILED DESCRIPTION OF THE INVENTION

The present technique for MR compatibility of an implanted electronic medical device considers several effects of direct current (DC) magnetic fields, gradient magnetic fields, and RF fields on patient safety, the implanted device and the MRI scanner. As a consequence, the medical device incorporates one or more mechanisms that offer high impedance to currents induced by the MRI electromagnetic fields or prevent such currents from forming in the first place. These mechanisms comprise non-ferromagnetic components which have a magnetic susceptibility close to that of the surrounding tissue; electrical leads with traps for MRI induced currents, and a housing formed by a plurality of electrically conductive segments that combine to provide RF shielding of internal circuit while not providing large enough areas for formation of eddy currents. As used herein, a "trap" is a circuit element that either or blocks current induced by the MRI fields or significantly attenuates that currents to a level at which the current does not cause an adverse effect to the animal being scanned.

The cable traps are placed along the cable to provide high impedance to radio frequency currents induced in the cable while presenting low impedance to direct current of stimulation pulses produced by the medical device. Such traps provide sufficiently high impedance, reactance and/or resistance, to prevent induced current from forming during MRI RF pulses in the 1-500 MHz range.

A terminating element at the lead to stimulator circuit interface, which provides high impedance at the gradient rise time frequency (1-10 KHz), but low impedance at the frequency of the generated pulses or sensed cardiac signal, eliminates currents induced on the lead by the E-field produced by the gradient coils in the MRI system. A preferred embodiment employs parallel resonant networks, such as bazooka baluns, to prevent standing waves on the shield of the cable. As an alternative to a balun, at least one PIN diode is placed along the cable and selectively forward and reverse biased by a DC control voltage to act as a switch. The PIN diode is rendered conductive during stimulation pulses produced by the medical device and is non-conductive at other times. A micro electromechanical system (MEMS) is another type of switch that can be used. The DC leads also need to present high impedance at the RF frequency, which can be accomplished via chokes or resistors, if the diode or MEMS switch uses low current.

The metallic housing, for the medical device's electronic circuitry, is separated into a plurality of overlapping electrically conductive segments that are insulated from one another. The result is a housing that offers high impedance for signals up to 200 KHz and acts as a continuous shield for RF signals in 1-500 MHz range. The RF shielding is due to the capacitance coupling between the electrically conductive segments.

Figure 1:
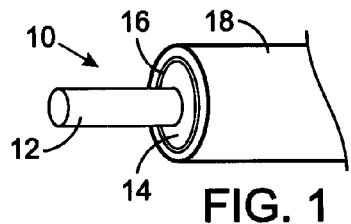
FIG. 1 is an isometric view of a conventional coaxial cable.

With initial reference to FIG. 1, a conventional coaxial cable 10 includes a center conductor 12 surrounded by a cylindrical enclosure 14 of a suitable dielectric material. A cylindrical electrically conductive shield 16 that surrounds the cylindrical enclosure 14 and is encased in an insulating outer cover 18.

Figure 2:
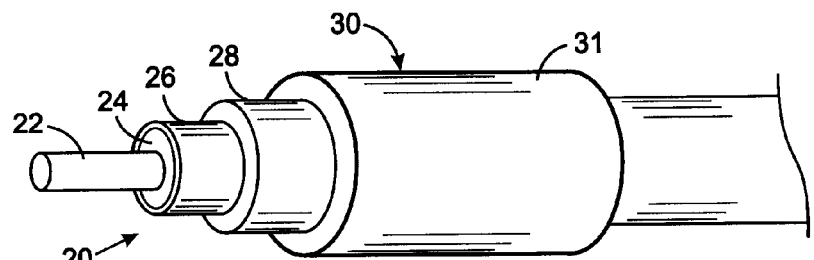
FIG. 2 is an isometric view of a tri-axial cable that has been modified with novel traps to prevent interaction with external RF fields of an MRI scanner.

FIG. 2 illustrates a modification of a standard tri-axial cable according to the present invention to form a coaxial cable with traps for signals induced in the cable by an MRI scanner. The traps impose high impedance to the common mode current induced in the cable by the E-field of an MRI radio frequency body coil. The modified tri-axial cable 20 comprises a central, first conductor 22 surrounded by a first tubular insulator 24 of a conventional dielectric material. A tubular second conductor, or inner shield, 26 extends around the first tubular insulator 24 to form an inner shield and is in turn surrounded by a second tubular insulator 28 of the dielectric material.

A standard tri-axial cable further comprises a tubular outer shield 32 of an electrically conductive material extending around the second tubular insulator 28 for the entire length of the cable. The resultant coaxial structure is encased in an insulating outer cover.

Figure 3:
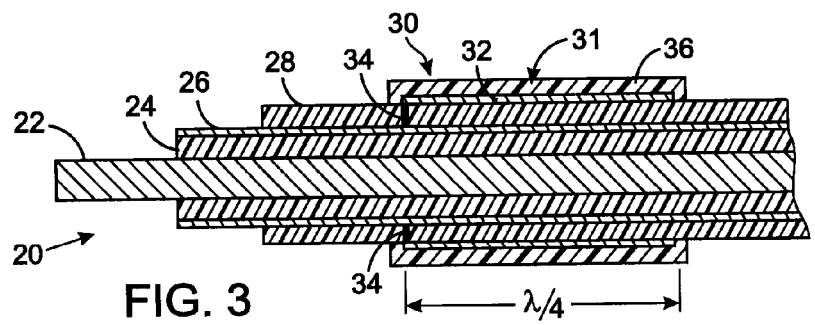
FIG. 3 is a longitudinal cross section of a portion of the tri-axial cable.

The tri-axial cable 20 in FIGS. 2 and 3 is a standard cable tri-axial that has been modified by cutting the tubular outer shield 32 and outer insulating cover 36 into a series of short sections. Those sections form traps 30 for common mode current induced in the cable by an MRI scanner. In the preferred embodiment of FIG. 3, each trap 30 comprises a bazooka balun 31 connected to the remaining cable layers, thereby forming a parallel resonant network connected to a two conductor coaxial cable. The electrically conductive tubular outer shield 32 is cut to a longitudinal length that is identical to one-quarter of the wavelength ($\lambda/4$) of an RF frequency for which immunity is desired. This is an RF frequency emitted by the magnetic resonance scanner. As will be described, the cut sections of the outer shield 32 form networks each having an inductor connected in parallel with a capacitor, wherein the LC networks are tuned to different MRI frequencies. One end of each outer shield section is shorted by shunts 34 to the tubular second conductor 26, and the opposite section end is disconnected from the first and second conductors 22 and 26. This forms a standard bazooka balun 31 that is attached to the remaining cable elements 22-28 which function as a coaxial cable. The second tubular insulator 28 now also serves as the outer covering of that coaxial cable. The insulating outer cover 36 encloses the tubular outer shield 32 and preferably has its ends sealed to the second tubular insulator 28 to prevent short circuits.

A bazooka balun is preferred for devices for implantation in vasculature of an animal, since the compact diameter of a tri-axial cable occupies relatively small volume of a blood vessel. However, other types of baluns could be used as the traps depending on the intended location of the cable. Examples of other baluns include a cable trap balun, where the cable is looped as a solenoid, and a parallel capacitance connects the grounds before and after the solenoid, thus forming a parallel resonator with high impedance at the frequency of interest. The bridge or lattice balun consisting of a network of two capacitors and two inductors also may be used.

Figure 4:
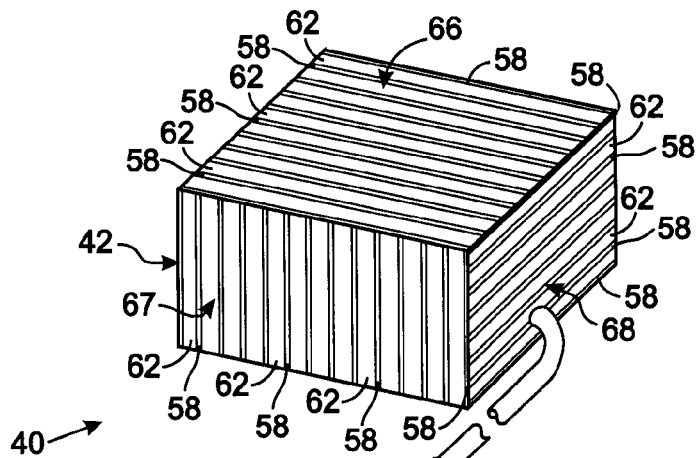
FIG. 4 illustrates the cable extending from a medical device housing to stimulation electrodes.

FIG. 4 shows a modified tri-axial cable 20 used as a lead for stimulation electrodes of an implantable medical device 40, such as a cardiac pacemaker or defibrillator. The medical device 40 has electronic circuitry contained in a housing 42 from which a modified tri-axial cable 44 extends. That cable 44 has a plurality of bazooka baluns 45, 46 and 47 with coaxial cable sections 48 and 49 located there between. At the remote end of the cable 44 from the housing 42, the central, first conductor 22 and the second conductor 26 are exposed to form bipolar electrodes for applying DC stimulation pulses to the tissue of the animal in which the device is implanted. Alternatively the central, first conductor 22 and the second conductor 26 can be connected to other forms of electrodes that are adapted for placement in or against particular anatomical features of the animal.

Alternatively, each trap 30 can be formed by a choke placed along the cable at intervals equal to a quarter wavelength ($\lambda/4$) determined by the Larmor frequency (e.g. 64 MHz at 1.5 T) of the MRI scanner. The chokes impose a high impedance at radio frequencies, but low impedance to DC.

Figure 5:
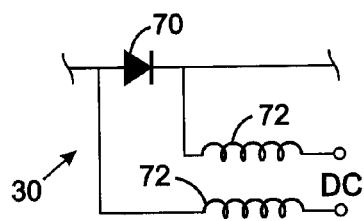
FIG. 5 is a schematic diagram of a second type of trap for the cable.

If a high degree of isolation of the cable to MRI induced currents is desired, PIN diodes 70 can be placed at quarter wavelength intervals along the cable. As shown in FIG. 5, each PIN diode 70 is forward biased by a DC control voltage during a stimulation pulse and reverse biased by that DC control voltage when RF immunity is desired, such as during MRI scan pulses. This embodiment requires additional cable conductors that are decoupled by chokes 72 and consume power from the medical device to bias the PIN diodes during long time periods.

Figure 6:
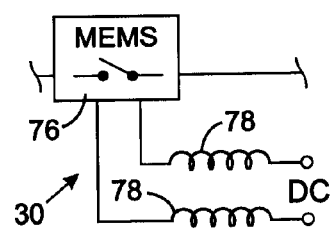
FIG. 6 is a schematic diagram of a third type of trap for the cable.

A further alternative, that provides a high degree of isolation, places a standard micro electro-mechanical system (MEMS) switch 76 at each trap location along the cable as depicted in FIG. 6. The MEMS is a miniaturized RF switch that does not requires a large current to close, unlike the large forward bias current required for a PIN diode. However, additional cable conductors and decoupling chokes 78 still are required. Due to the low power consumption of the MEMS, resistive wire may be used to supply the MEMS with DC.

Figure 7:
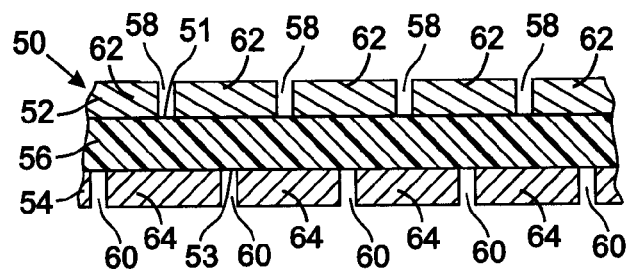
FIG. 7 is a cross section through a wall of a medical device housing and shows detail of slots in conductive layers that prevent formation of gradient eddy currents.

Referring to FIGS. 4 and 7, the housing 42 of the implantable medical device 40 also has been uniquely constructed to be compatible with an MRI scanner. FIG. 7 shows a cross section through one exterior walls 66 of that housing 42. The wall is electrically conductive to shield the internal electronic circuitry from radio frequency interference during normal operation. Specifically, the housing walls are conductive at RF frequencies, but have a high impedance at the frequency associated with the leading and trailing edges of the MRI gradient pulses, thus preventing gradient eddy currents in the walls. The exemplary wall 66 is formed by outer conducting layers 52 and 54 of aluminum, copper, or other electrically conductive, non-ferromagnetic material applied to the major surfaces of a substrate 56 of dielectric material, thereby forming a laminated wall with the substrate sandwiched between two conductive layers. The first layer 52 is on the exterior surface 51 of the substrate 56, and the conducting second layer 54 is on the interior surface 53 of the substrate.

A plurality of slots 58 and 60 are made through the first and second layers 52 and 54, respectively, to expose dielectric substrate 56, thus creating a plurality of conductive segments 62 and 64 which form stripes on the opposing surfaces of the substrate 56. The first slots 58 in the first layer 52 are offset in the plane of the wall from the second slots 60 in the second layer 54 so that there is not a direct electrical path through both layers 52 and 54. RF continuity is ensured via the capacitance coupling created through the dielectric substrate 56 between opposing conductive segments 62 and 64. The spacing between the slots on each dielectric surface is a function of the slew rate or rise time of the MRI gradient signal. Shorter rise times of the gradient pulses require smaller metallic surfaces to keep gradient eddy currents to an acceptable predefined level which will not adversely affect the animal. For example, a typical MRI gradient signal pulse requires each conductive segments 62 and 64 to be ten square centimeters or less.

With respect to FIG. 4, note that the slots 58 in one wall 66 of the housing 42 are not aligned with nor parallel to the slots 58 in an adjacent abutting wall 67 or 68. The same is true for the hidden walls in the drawings. A slot 58 also extends along each corner of the housing where two walls meet, so that the conductive segments 62 in the walls are not electrically connected. The same misalignment exists on the interior surfaces of the walls.

Figure 8:
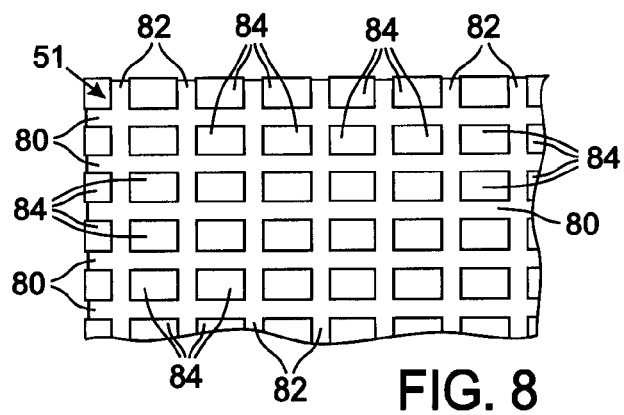
FIG. 8 is a plane view of an alternative configuration of slots in the surface of the medical device housing.

FIG. 8 illustrates an alterative arrangement of the slots in the outer surface 51 of the housing 42. A first group of slots 80 extend transversely, preferably orthogonally, to a second group of slots 82, thereby forming a two dimensional array of conductive segments 84 in the electrically conductive first layer 86. A similar arrangement of transverse groups of slots form another two dimensional array of conductive segments on the second layer that forms the interior surface of the wall. The exterior and interior arrays are offset in both directions to overlap thereby capacitively coupling the first and second layers.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

The invention claimed is:

1. An implantable medical device that is compatible with a magnetic resonance imaging scanner, said implantable medical device having an electronic circuit and comprising:
a housing containing the electronic circuit and having a plurality of exterior walls, wherein each exterior wall comprises a substrate of an electrically non-conductive, dielectric material with opposing first and second surfaces, a first layer of electrically conductive material on the first surface, and a second layer of electrically conductive material on the second surface, wherein the first layer includes a plurality of first slots which expose the dielectric material and divide the first layer into a plurality of first segments, and a plurality of second slots in the second layer which expose the dielectric material and divide the second layer into a plurality of second segments.

2. The implantable medical device as recited in claim 1 wherein the first segments and second segments inhibit eddy currents from being induced in those segments due to one or more fields of the magnetic resonance imaging scanner.

3. The implantable medical device as recited in claim 1 wherein the first segments and second segments are sized to restrict eddy currents from being induced therein by one or more fields of the magnetic resonance imaging scanner.

4. The implantable medical device as recited in claim 1 wherein the plurality of first slots is non-parallel to the plurality of second slots.

5. The implantable medical device as recited in claim 1 wherein the plurality of first slots comprises a first group of slots and a second group of slots extending transverse to the first group.

6. The implantable medical device as recited in claim 5 wherein the second group of slots extends orthogonally to the first group of slots.

7. The implantable medical device as recited in claim 5 wherein the plurality of second slots comprises a third group of slots and a fourth group of slots extending transverse to the third group.

8. The implantable medical device as recited in claim 1 wherein the housing has a first exterior wall and a second exterior wall abutting the first exterior wall and the slots in the first exterior wall are misaligned with the slots in the second exterior wall.

9. The implantable medical device as recited in claim 1 wherein the housing has a first exterior wall and a second exterior wall abutting the first exterior wall and the slots in the first exterior wall are non-parallel to the slots in the second exterior wall.

10. The implantable medical device as recited in claim 1 wherein the slots in each exterior wall are non-parallel to the slots in adjacent exterior walls of the housing.

11. The implantable medical device as recited in claim 1 further comprising a cable extending from the housing, wherein the cable comprises a first conductor, a second conductor and a plurality of traps connected to the second conductor at intervals along the cable, each trap mitigating electrical current induced in the cable by one or more fields of the magnetic resonance imaging scanner.

12. The implantable medical device as recited in claim 11 wherein the second conductor extends coaxially around the first conductor and further.

13. The implantable medical device as recited in claim 12 wherein the each trap comprises a tubular third conductor extending coaxially around the second conductor and having one end that is connected to the second conductor.

14. The implantable medical device as recited in claim 11 wherein the each trap comprises a balun.

15. The implantable medical device as recited in claim 11 wherein the each trap comprises one of a choke, a bazooka balun, a micro electro-mechanical system switch, and a PIN diode.

16. The implantable medical device as recited in claim 1 wherein the electrically conductive material of the first layer and second layer has a magnetic susceptibility that is substantially identical to the magnetic susceptibility of tissue of an animal in which the medical device is adapted for implantation.

17. An implantable medical device that is compatible with a magnetic resonance imaging scanner, said implantable medical device comprising:
a housing containing an electronic circuit and having a plurality of exterior walls with opposing first and second sides, wherein each exterior wall comprises a plurality of electrically non-conductive segments on the first side interleaved with and offset from a plurality of electrically conductive segments on the second side, thereby creating two wall surfaces that substantially attenuate eddy currents at frequencies less than 200 KHz which are induced in the wall surfaces by one or more fields of the magnetic resonance imaging scanner, wherein capacitive coupling between the electrically conductive segments renders the wall surfaces conductive to currents at frequencies above 1.0 MHz; and a cable extending from the housing, wherein the cable comprises a first conductor, a second conductor, and a plurality of traps connected to the second conductor at intervals along the cable, each trap mitigating electrical current induced in the cable due to one or more fields of the magnetic resonance imaging scanner.

18. The implantable medical device as recited in claim 17 wherein the second conductor extends coaxially around the first conductor.

19. The implantable medical device as recited in claim 18 wherein the each trap comprises a tubular third conductor extending coaxially around the second conductor and having one end that is connected to the second conductor.

20. The implantable medical device as recited in claim 17 wherein the each trap comprises a balun.

21. The implantable medical device as recited in claim 17 wherein the each trap comprises one of a choke, a bazooka balun, a micro electro-mechanical system switch, and a PIN diode.

22. The implantable medical device as recited in claim 1 wherein each exterior wall has opposing edges, each of the plurality of first segments extend from one opposing edge to another opposing edge and each of the plurality of second segments extend from one opposing edge to another opposing edge.

23. The implantable medical device as recited in claim 17 wherein each exterior wall has opposing edges, and each of the plurality of electrically non-conductive segments on the first side and each of the plurality of electrically conductive segments on the second side extend from one opposing edge to another opposing edge.

* * * * *